(12) United States Patent
Chase (10) Patent No.: US 6,227,807 B1
(45) Date of Patent: May 8, 2001

(54) CONSTANT FLOW FLUID PUMP

(76) Inventor: Eric Chase, 1312 Chesterton Way, Walnut Creek, CA (US) 94596

( * ) Notice: Subject to any disclaimer, the term of this patent is extended or adjusted under 35 U.S.C. 154(b) by 0 days.

(21) Appl. No.: 09/241,654

(22) Filed: Feb. 2, 1999

(51) Int. Cl.$^7$ .................................................. F04B 49/06
(52) U.S. Cl. .......................... 417/44.1; 417/36; 417/46; 210/634
(58) Field of Search .................... 210/656, 634; 318/685; 417/20, 478, 38, 22, 44, 44.1, 44.3, 46, 2, 36

(56) References Cited

U.S. PATENT DOCUMENTS

| | | | |
|---|---|---|---|
| 3,855,515 | * 12/1974 | Hutchins, Jr. | 318/685 |
| 3,985,467 | * 10/1976 | Lefferson | 417/20 |
| 4,236,880 | * 12/1980 | Arcibald | 417/478 |
| 4,242,051 | * 12/1980 | Mason et al. | 417/38 |
| 4,352,636 | * 10/1982 | Patterson et al. | 417/22 |
| 4,599,046 | * 7/1986 | James | 417/44 |
| 4,775,481 | * 10/1988 | Allington | 210/656 |
| 4,913,624 | * 4/1990 | Seki et al. | 417/2 |
| 4,990,058 | * 2/1991 | Eslinger | 417/46 |
| 5,520,517 | * 5/1996 | Sipin | 417/44.3 |
| 5,866,004 | * 2/1999 | Houck et al. | 210/634 |
| 5,915,925 | * 12/1999 | North, Jr. | 417/36 |

* cited by examiner

Primary Examiner—Teresa Walberg
Assistant Examiner—Leonid Fastovsky (57) ABSTRACT

The present invention is a means and method for providing constant output flow from a fluid pump. The invention does this by controlling the radial speed of the pump motor during discreet segments of the motor's 360° angular/radial path through a revolution of the pump. The electric pump motor is controlled throughout the 360° radial path by employing a control means for controlling the speed of actuation of the radial steps of a stepper motor throughout the 360° path of rotation of the stepper motor. Control means for controlling the speed of the discreet steps of the stepper motor comprises at least a memory means, a counting means and an amplification means.

12 Claims, 7 Drawing Sheets

CONSTANT FLOW FLUID PUMP

BACKGROUND OF THE INVENTION

1. Field of the Invention

The invention relates in general to a constant flow fluid pump and in particular to means and method for reduction of pressure and flow pulsations in a fluid pump by selectively controlling the rotational speed of the pump driving motor at any one of a predetermined number of discrete rotational steps around the 360° periphery of the driving motor rotation.

2. Description of the Related Art

There are many applications for analyzing blood and other fluids for which it is important to move the fluid to be examined at a uniform rate through testing/analyzing equipment, such as a flow cytometer. These fluids are usually driven by a constant pressure source. However the application of a constant pressure to a fluid may not result in a constant flow if the resistance to flow changes. For constant flow, the force pumps for driving these fluids are either of the diaphragm or reciprocating piston type of positive displacement pump that is actuated by an electric motor.

A problem with positive displacement pumps is that the rotary displacement of the electric motor must be converted to a linear displacement in order to activate the pump and thereby pump the fluid, i.e., both the diaphragm and the reciprocating piston are driven by a powered rod of some type that receives its linear motion by means of a reciprocating crankshaft. Whether it be a diaphragm pump or a reciprocating piston pump, the linear actuated rod must have its power converted from the rotary motion of the motor by means of a crankshaft/driving rod arrangement. It is well known that the output of a rotary motor driving a rod through a crankshaft arrangement, has a sinusoidal displacement output. The driving rod experiences displacement variations ranging from a minimum of zero at both top dead center and bottom dead center of its rotation through the crankshaft journal to a maximum displacement midway between top dead center and bottom dead center. It is also well understood in the Art that other parameters of the output pump also experience the same sinusoidal variation through the 360° rotation of the driving motor through the crankshaft/driving rod arrangement. For example, it is well-known that the pressure and the flow output of both a diaphragm and a reciprocating piston pump consist of a half-rectified sine wave. If the pump is driving a purely resistive load, the pressure and flow will be in phase and have their maximum value when the crank of the pump is in the middle of its upstroke, at 90° away from top dead center (TDC). After the pump passes TDC, the flow and pressure go to zero for a purely resistive load until the crank reaches bottom dead center (BDC).

Positive displacement pumps of the leadscrew drive type can provide a constant flow independent of resistance. However they must be refilled during the downstroke, during which time there is no output flow. Dual acting positive displacement pumps of the leadscrew drive type operate in tandem, so that as one pump is supplying fluid, the other pump is refilling. However these types of double acting pumps are expensive and complex.

A flow cytometer requires a pulseless flow of sheath fluid to obtain precise particle measurements. Present flow cytometers, in order to compensate for the pressure/flow variation described above, use one of two methods known in the Art to apply a pulseless flow of sheath fluid. The first is the use of a pressurized tank of sheath fluid that will even out the pulsations and the second is the use of a compliant member such as for example compressing a static volume of air through a flexible membrane. The problems with these two compensation methods is that the tank must have a very small height to prevent pressure variations from occurring as the tank empties and the tank must be sturdy enough to withstand pressure of 5–10 PSI, and that a constant pressure source doesn't provide a constant flow if the resistance to flow changes. Furthermore, the sheath fluid becomes saturated with air, which may be released as micro bubbles at the flow cell, causing the detection of false particles. The second method is equally problematic in the use of flow cytometry as well as other fluids analytical instruments in that the compliant member often is large and unwieldy and sometimes several compliant members are necessary to smooth pulsations in the flow of sheath fluid. Accordingly, it would be desirable to have a fluid pump driven by an electric motor through a crankshaft/driving rod arrangement that would have as close to a constant pressure and fluid output as possible through the 360° rotational driving range of motion of the electric motor.

SUMMARY OF THE INVENTION

Briefly, the present invention is a means and method for controlling the output flow of a fluid pump. The invention does this by controlling the radial speed of the pump motor during discreet segments of the motor's 360° angular/radial path through a revolution of the pump. The electric pump motor is controlled throughout the 360° radial path by employing a control means for controlling the speed of actuation of the radial steps of a stepper motor throughout the 360° path of rotation of the stepper motor. Control means for controlling the speed of the discreet steps of the stepper motor comprises at least a memory means, a counting means and an amplification means. The memory means may be an EPROM or other memory device for storing a series of numbers, each number representing selective speeds for which the stepper motor rotates to desired positions. The counting means which may be for example a binary counter is for retrieving the discreet numbers from the memory means for each selective position speed. The amplifying means, which may be for example a bipolar constant current driver, takes the output control signal from the counting means and amplifies it and conditions it so that it is suitable for energizing the stepper motor to rotate at the selected discreet speed necessary to achieve the selected discreet position along the 360° rotation of the stepper motor output shaft.

The motor/pump combination of the invention provides a constant or near constant flow during the upstroke of the pump. Of course, every pump outputs no flow during the downstroke time. The constant flow motor/pump of the invention compensates for this by keeping the down stoke time to 1/30 of the upstroke time and provides a flow interruption filter to suppress this interruption of the flow during the upstroke. This flow interruption filter includes two compliant lengths of tubing separated by a resistive orifice.

BRIEF DESCRIPTION OF DRAWINGS

The invention may be understood and further advantages and uses thereof more readily apparent, when considered in view of the following detailed description of the exemplary embodiments, taken with the accompanying drawings in which.

DESCRIPTION OF PREFERRED EMBODIMENTS

Figure 1:
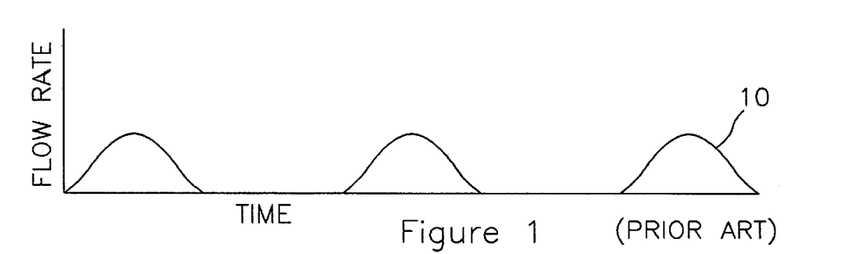
FIG. 1 is a graph of flow rate verses time for the prior art sinusoidal output of a rotary positive displacement pump driven by an electric motor.

Referring now to the drawings and to FIG. 1 in particular there is shown a graph 10 of the prior art sinusoidal output of a rotary positive displacement pump driven by an electric motor. Both the pressure and volume output of the pump are shown as a half rectified sine wave, which graph replicates the actual output experienced by displacement pumps of the prior art.

Figures 2, 2A:
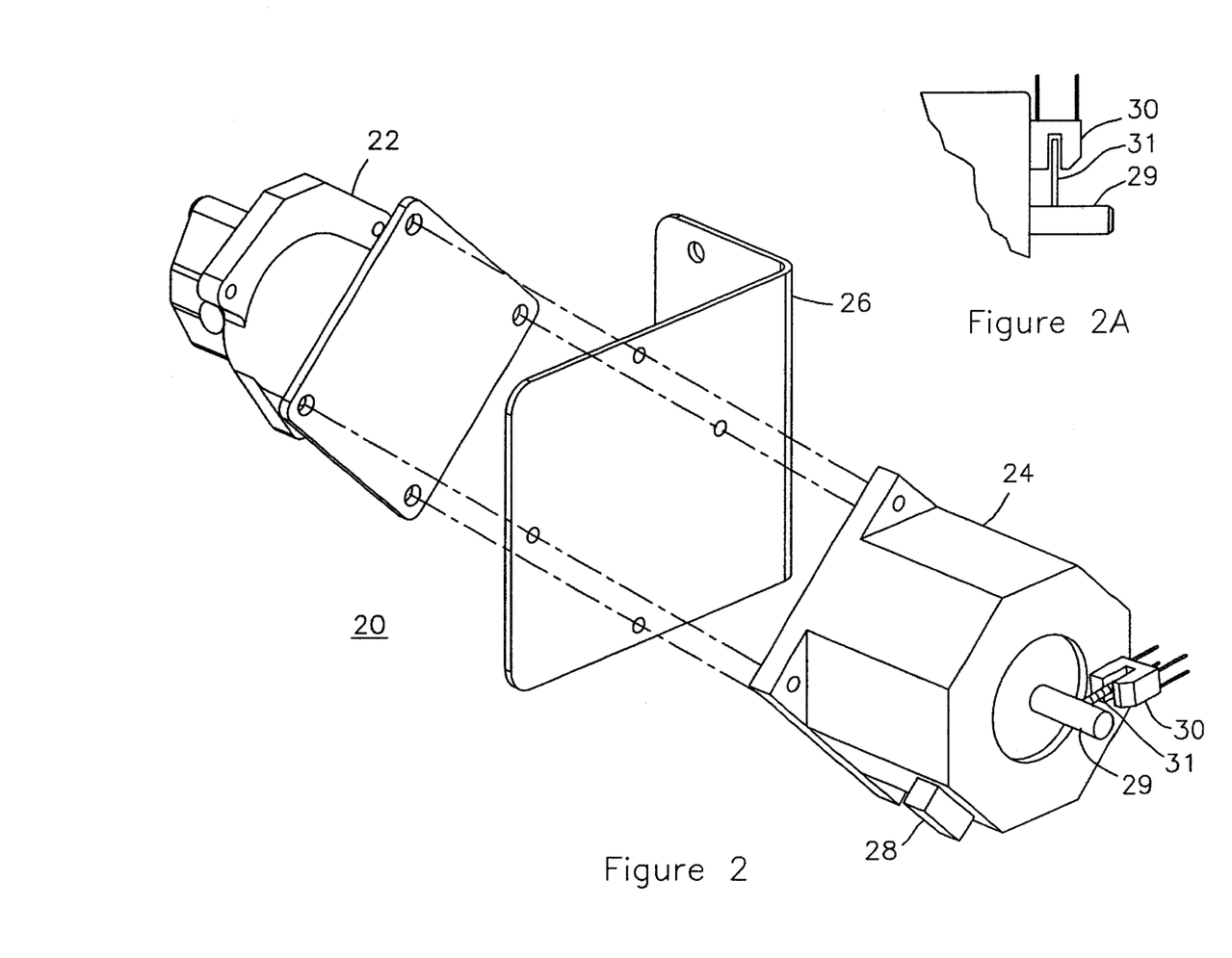
FIG. 2 is a pictorial view of a rotary positive displacement pump driven by a stepper motor, constructed according to the teachings of the invention.
FIG. 2A is an enlarged top plan view of the reset sensing means with rotating flag shown in FIG. 1.

Referring now to FIGS. 2 and 2A there are shown pictorial views of a rotary positive displacement pump unit 20 constructed according to the teachings of the invention. Pump unit 20 includes positive displacement pump 22, mechanically coupled with and driven by stepper motor 24, having mounting bracket 26 disposed there between. Stepper motor 24 is adapted for connection to outside electrical power by means of electrical connector 28. Electrical power supplied to stepper motor 24 is conditioned by a control means of the invention so as to control the output of pump 22 to replicate as closely as possible a constant step function of both pressure and flow (volume per unit time). A full rotation of motor shaft 29 is sensed by sensing means 30, which may be for instance an optical proximity sensor, when shaft flag 31 passes there through.

Figure 3:
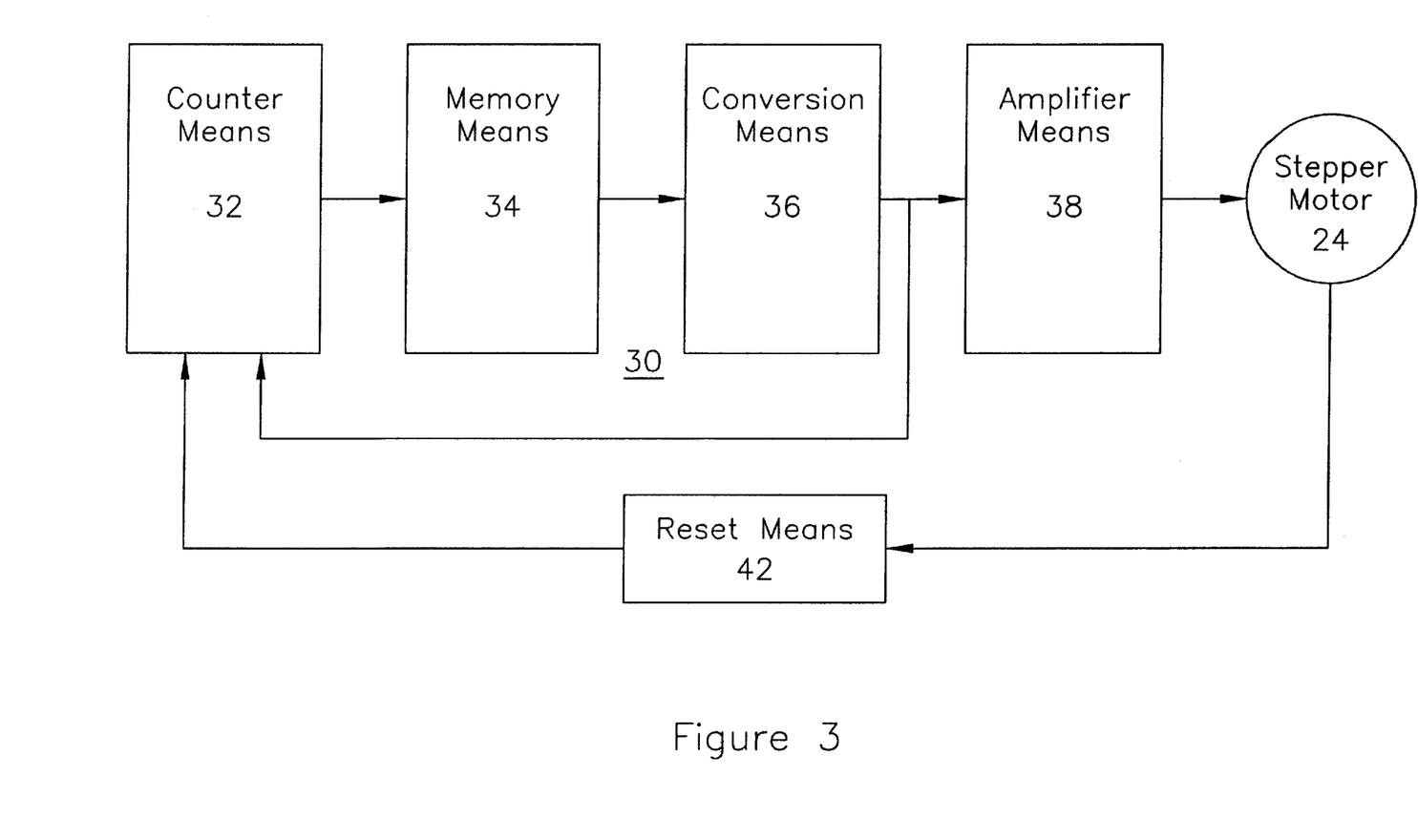
FIG. 3 is a block diagram of the control means for controlling the angular velocity/speed of the stepper motor of FIG. 2.
Figure 4A:
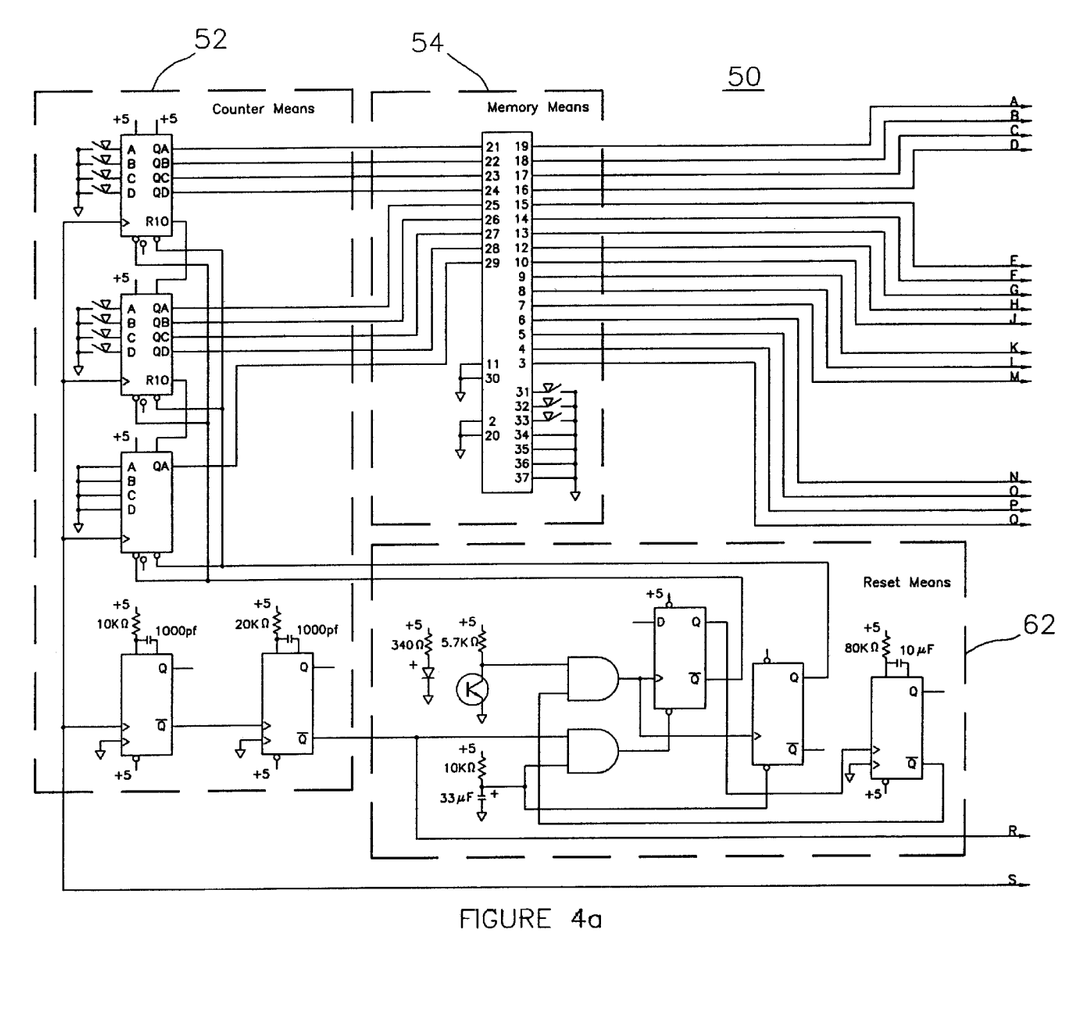
FIGS. 4A and 4B are a schematic view of the wiring diagram for the control means for controlling the angular velocity/speed of the stepper motor of FIG. 2.

Referring now to FIG. 3 there is shown a block diagram 30 of the control means for controlling the angular velocity/speed of the stepper motor 24 of FIG. 2 through 400 half step output positions. Likewise referring now to FIGS. 4A and 4B there are shown a corresponding schematic view of the electronic circuit and wiring diagram for the control means for controlling the angular velocity/speed of the stepper motor of FIG. 2. FIGS. 3 and 4A,B have a one to one correspondence between their respective blocks in FIG. 3 and the directly corresponding individual electronic circuits shown in phantom boxes in FIGS. 4A and 4B. Block diagram 30 includes counter means 32, memory means 34, conversion means 36, amplification means 38 and reset means 42. Likewise electronic circuit and wiring diagram 50 includes counter means circuit 52 which corresponds directly with counter means block 32 of block diagram 30; memory means circuit 54 which corresponds directly with memory means block 34 of block diagram 30; conversion means circuit 56 which corresponds directly with conversion means block 36 of block diagram 30; amplification means circuit 58 which corresponds directly with amplification means block 38 of block diagram 30; and reset means circuit 62 which corresponds directly with reset means block 42 of block diagram. Of course both electronic circuit 50 and block diagram 30 control stepper motor 24 which is shown only in block diagram 30.

Description/Function of Stepper Motor Control System

Figure 4B:
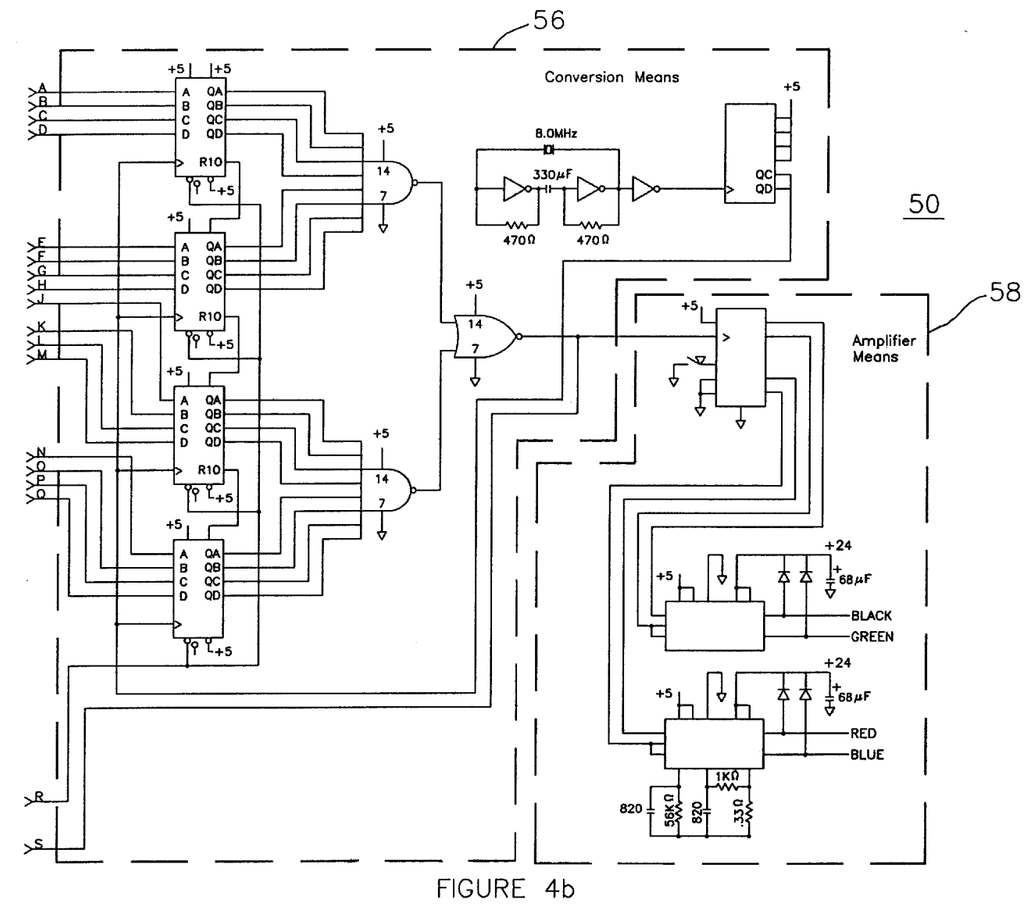

Referring now to FIGS. 3 and 4, there will be described the description/function of the individual blocks of block diagram 30 and their directly corresponding individual circuits of electronic circuit 50.

Counter Means: The counter means 32 counts the number of half steps taken by the motor 24, and sends this count to the Memory Means 34. The counter advances 400 steps during 1 revolution, and then is reset by the Reset Means 42.

Memory Means: The memory means 34 contains 400 numbers, each number representing the velocity of the motor 24 at each of the 400 steps. The specification of which of the 400 numbers to access is provided by the counter means 32 and the number is output to the conversion means 36.

Conversion Means: The conversion means 36 takes the number from the memory means 34 representing the motor velocity, and loads the number into an internal conversion means counter. The internal conversion means counter then counts down to zero at a constant rate. When the internal conversion means counter reaches zero, a pulse is output to the Counter Means 32 to advance the counter means 32 by 1, and to the Amplifier Means 38 to advance the stepper motor 24 by half a step. Note that larger numbers provided to the Conversion Means 36 represent slower velocities, since the time required to count to zero is longer.

Amplifier Means: The pulse from the Conversion Means 36 causes the amplifier means 38 to advance the stepper motor 24 by half a step. Reset Means: Once per revolution, an optical sensor 30 which may be mounted on the stepper motor 24 sends a signal to the Counter Means 32 when flag 31 passes there through (FIGS. 2 and 2A) that resets the count. If the stepper motor 24 has missed a step during the prior revolution, the counter means will be resynchronized with the actual position of the stepper motor at this point.

Figure 5:
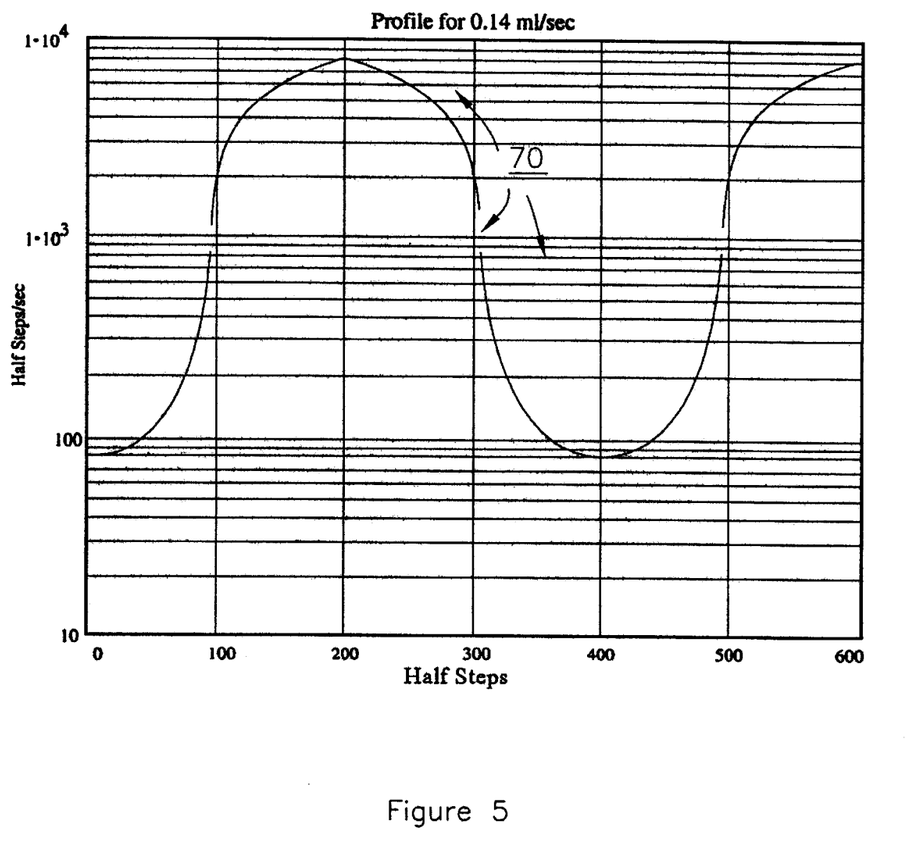
FIG. 5 is a graph of the non-sinusoidal angular velocity (in half steps/second verses motor position in half steps) of the rotary positive displacement pump stepper motor constructed according to the teachings of the invention.

Referring now to FIG. 5 there is shown a graph 70 of the non-sinusoidal angular velocity output of the rotary positive displacement pump 22 driven by a stepper motor 24, constructed according to the teachings of the invention. Steps 0–99 are the second half of the upstroke, steps 100–199 are the first half of the downstroke, steps 200–299 are the second half of the downstroke, and steps 300–399 are the first half of the upstroke. To maintain a constant upstroke velocity between steps 0–99, the motor's rotational velocity must become very large as it approaches the end of the upstroke. This requires a very large acceleration. The torque required to achieve this acceleration must be compared to the torque available from the motor. At some point near the end of the upstroke, the acceleration will be limited by the torque available from the motor. With moderately sized stepper motors, this limitation occurs at around step 95. So between steps 0–95, a constant flow profile is maintained, and between steps 96–100, the flow profile is torque limited.

The downstroke time, from steps 100–299, must be minimized. Therefore, to accomplish this, acceleration is maximized between steps 100–199, and deceleration is maximized between steps 200–299. The maximum available motor torque is determined at each step, and then the maximum acceleration or deceleration is determined. With a moderately sized stepper motor, the downstroke requires a period of about 58 milliseconds.

Lastly, to maintain a constant upstroke velocity between steps 300–399, the motor must be rapidly decelerated as it enters the beginning of the upstroke to maintain a constant upstroke velocity. Again, the torque required to achieve this deceleration must be compared to the torque available from the motor. The deceleration is torque limited between steps 300–305, and a constant flow profile is maintained between steps 306–399. The process is then repeated starting with step 0.

The speed of the individual steps as shown on graph 5 in half steps per second will be calculated by means of a stepper pump profile calculation.

Stepper Pump Profile Calculation
Calculate 2nd half upstroke (400 steps/revolution, so 100 steps for second half upstroke)
  For i=0 to 99 do
    Steps/sec=A/sin(B*i) [where A and B are constants representative of and derived from the stroke volume of the pump 72 (FIG. 2) and desired flow rate to the load 82 (FIG. 7), respectively]
    Calculate torque required for next step acceleration
    Compare to torque available from motor at this speed
    Limit acceleration if necessary
    Convert steps/sec to counter counts
    Write counter counts to profile file and store in Memory Means 34
Calculate 1st half downstroke
  For i=100 to 199 do
    Calculate maximum torque available from motor at steps/sec
    Subtract torque required to overcome friction to determine torque available for acceleration
    Calculate maximum increase in steps/sec using torque available for acceleration
    Calculate new steps/sec
    Convert steps/sec to counter counts
    Write counter counts to profile file and store in Memory Means 34
Calculate 2nd half downstroke
  For i=200 to 299 do
    Steps/sec[i]=steps/sec[400−i] for mirror image of 1st half downstroke
    Write counter counts to profile file and store in Memory Means 34
Calculate 1st half upstroke
  For i=300 to 399 do
    Steps/sec[i]=Steps/sec[400−i] for mirror image of 2nd half upstroke
    Write counter counts to profile file and store in Memory means 34.

Figure 6:
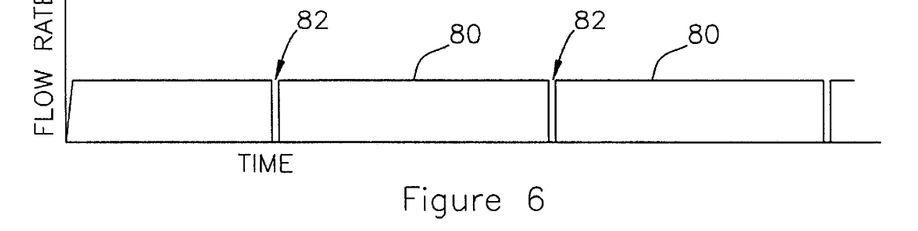
FIG. 6 is a graph of flow rate verses time of the rotary positive displacement pump driven by the stepper motor, all constructed according to the teachings of the invention.

When the pump has been driven by the motor at the motor velocity shown in FIG. 5, the flow rate verses time of the graph shown in FIG. 6 is the resulting output. Please note the flat, constant step function portions 80 that represent the upstroke portion of the motor/pump rotation and the interruptions 82 to this constant step function 80 that represent the downstroke portions of the motor/pump rotation. The teachings of the invention endeavor to minimize these interruptions 82, with the ideal condition of eliminating these downstroke interruptions altogether. This is accomplished according to the teachings of the invention by the use of a filtering means.

Figure 7:
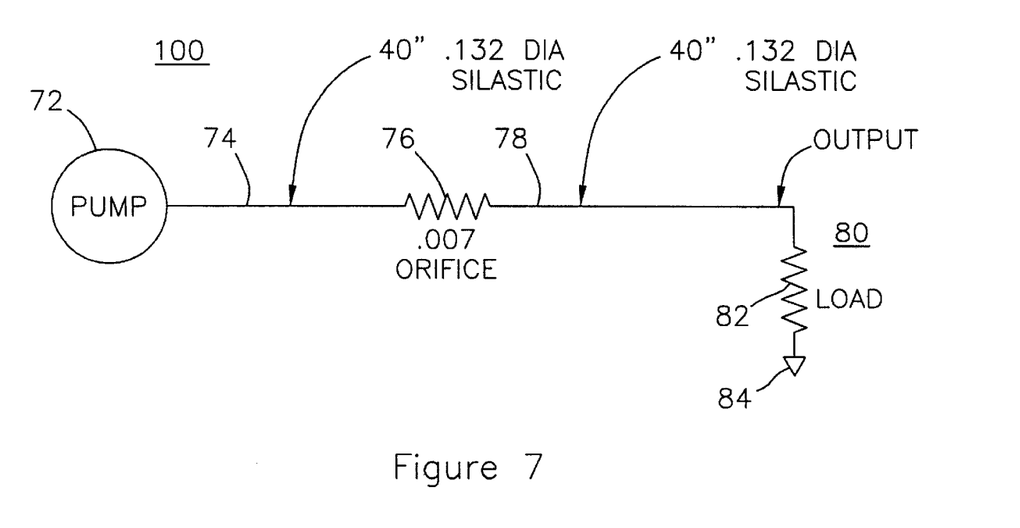
FIG. 7 is a schematic drawing of the output filter apparatus that is placed in series with the output flow or the rotary positive displacement pump of the invention to minimize the flow interruption when the motor is turning the pump in the downstroke positions.

Referring now to FIG. 7, there is shown a schematic drawing of the output filter apparatus 100 that is placed in series with the output flow of the rotary positive displacement pump of the invention to minimize the flow interruption when the motor is turning the pump in the downstroke portion of the cycle.

Pump 72's output is fed through two elastic members 74, 78 respectively, and a resistive member 76, which together with load 82, comprise filter apparatus 100. Elastic members 74,78 may be for instance, 0.132 diameter Silastic tubing and resistive member 76 may be for instance, a 0.007 inch orifice. 80 represents the output flow after passing through the elastic and resistive members, 82 represents the load and 84 is atmosphere.

Figure 8:
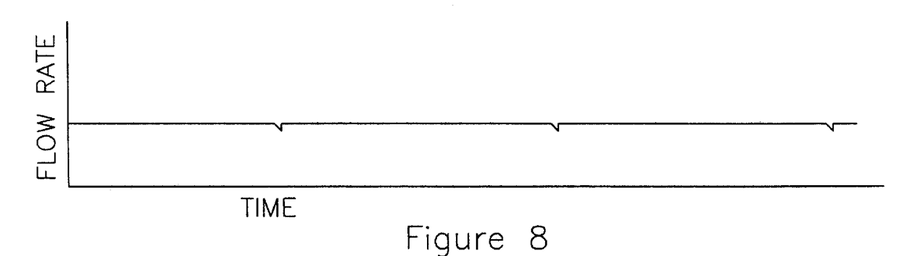
FIG. 8 is a graph of flow rate verses time after the flow output from the rotary positive displacement pump of the invention passes through the filter apparatus of FIG. 7.

FIG. 6 shows the output of pump 72 without the benefit of Filter apparatus 100 and FIG. 8 shown the output of pump 72 with filter apparatus 100. It is evident that the flow 80 is nearly constant (to approximately 0.2% of the flow rate's original amplitude).

In conclusion, what has been disclosed is means and methods for changing the analog motion of an electric motor to a digital representation both in the profile and in the actual performance, i.e., the positioning, of the electric motor by means of the motor control system of the invention coupled with a standard stepper motor that is available in the art. The flow profile shown in FIG. 6 has a constant flow during the upstroke, but no flow during the downstroke. Although the downstroke time is only 1/30 of the upstroke time in this embodiment of the invention, this interruption of flow is not desirable in flow applications, for which the invention was developed. In order to suppress this interruption of the flow rate, compliant tubing and a resistive orifice can be added to the output of the pump. FIG. 7 illustrates the filter configuration used to suppress the interruptions of flow shown in FIG. 6. This filter consist of two compliant lengths of tubing separated by a resistive orifice. In this particular embodiment of the invention, the flow rate decreases by only 0.2% during the downstroke, or conversely, the flow remains at 99.8% of its desires output during the downstroke, i.e. approximating the ideal conditions of eliminating the downstrokes altogether.

I claim:

1. A constant flow fluid pump, including a single fluid pump means having a single linear moving piston actuated by a rod and a crankshaft within a single cylinder for pumping a fluid through said single cylinder, comprising:
    a motor disposed in mechanical communication with said crankshaft of said single pump means; and
    control means in electrical communication with said motor for energizing said motor at predetermined differing rates at discrete steps through the 360° rotation of said motor to provide for rotating said crankshaft at fluctuating speeds and thereby drive said single moving piston at a constant linear speed during the upstroke of said single piston, and to minimize the drown stroke time of said single piston.

2. The constant flow pump of claim 1 wherein the control means energizes the motor at predetermined differing rates by supplying uniform current/power to the motor at predetermined differing times.

3. The constant flow pump of claim 2, wherein said control means includes memory means, counting means, converting means, amplifying means and reset means.

4. The constant flow pump of claim 3 wherein the memory means includes an EPROM programmed with a predetermined series of numbers each representing a different time between motor steps.

5. A means for controlling the linear speed of a piston rod that is being driven by a rotating crank shaft, comprising:

a) a stepper motor means in rotatable communication with said rotating crank shaft for turning said crank shaft in discreet steps throughout the full 360° rotation; and b) control means for controlling the predetermined incident speed of said stepper motor throughout said 360° rotation.

6. The means for controlling the linear speed of a rod driven by a reciprocating crank shaft of claim 1, wherein said control means further includes a preprogrammed forward control memory means for storing a series of numbers, each of said numbers being representative of a discreet signal to said stepper motor to articulate a discreet step in said 360° rotation of said stepper motor, a counting means for selecting the numbers stored in said memory means, a conversion means for converting said number to a time interval before the next step command is given, and a driving means responsive to the output step command signals of said conversion means for outputting electrical power to said stepper motor for energizing said stepper motor to articulate the next step for each of said steps around said 360° rotation.

7. A control means for converting a position controlled device into a speed controlled device, comprising:

a) a memory means for storing a series of numbers, each of said numbers being representative of a discreet signal to a stepper motor to articulate a discreet step in the 360° rotation of said stepper motor and the speed of articulating said discreet step;

b) a counting means for selecting the numbers stored in said memory means, a conversion means for converting said numbers to a time interval before the next motor step and for outputting a signal representative of the incidence of the discreet step of said stepper motor of said 360° rotation; and c) a driving means responsive to the output signals of said conversion means for outputting electrical power to said stepper motor for energizing said stepper motor to articulate each of said steps around said 360° rotation.

8. The constant flow pump of claim 3 wherein the memory means includes means for storing 400 numbers, each number representing the velocity of the motor at each of 400 discrete steps around the 360° rotation of the motor.

9. The constant flow pump of claim 8 wherein the counter means includes means for counting the number of half steps during which the motor has advanced, said counter means further includes means for counting the advancing 400 half step advances during one revolution of the motor prior to being reset by the reset means.

10. The constant flow pump of claim 9 wherein the conversion means further includes an internal conversion means and includes means for taking each of the 400 numbers representing motor velocity from the memory means and loading said number into said internal conversion means, said internal conversion means includes means for counting down from said number at a constant rate and outputting a pulse to the counter means for advancing the counter means by one step and for outputting a pulse to the amplifier means.

11. The constant flow pump of claim 10 wherein the amplifier means includes means to convert and amplify said conversion means pulse into suitable half step energization current for causing the motor to advance a half step.

12. The constant flow pump of claim 11 wherein the reset means includes an optical sensor means having a reset flag disposed on the motor so as to rotate with the motor's output shaft, which optical sensor means sends a reset signal to the counter means when said optical sensor means senses said reset flag, to provide for synchronizing said counter means with the actual position of the motor to provide for resetting the counter means when the piston is in the correct position within the cylinder at the beginning of the next stroke.

\* \* \* \* \*